Figure 1:
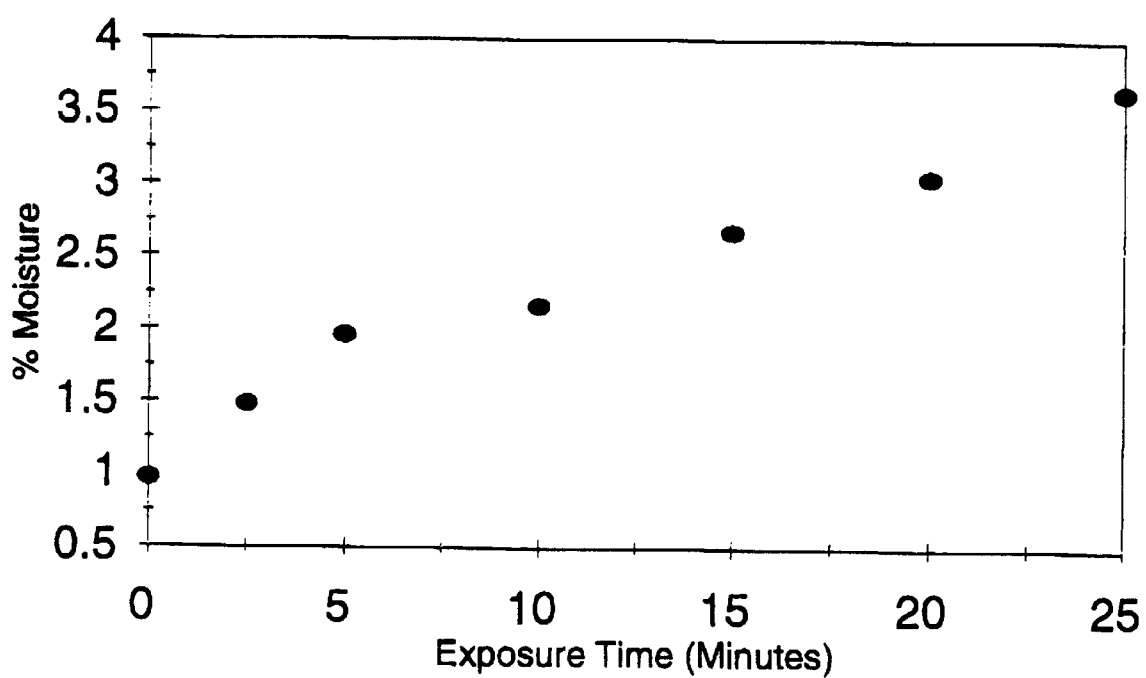

United States Patent [19]

Savage et al.

[11] Patent Number: 5,837,519

[45] Date of Patent: Nov. 17, 1998

[54] DRY-HEAT VIRAL INACTIVATION UNDER CONTROLLED MOISTURE CONDITIONS

[75] Inventors: Margaret Savage, Clayton; Juan Torres, Raleigh, both of N.C.

[73] Assignee: Bayer Corporation, Berkeley, Calif.

[21] Appl. No.: 749,354

[22] Filed: Nov. 21, 1996

[51] Int. Cl.$^6$ .............................. A01N 1/02; C12N 7/04
[52] U.S. Cl. ................................ 435/236; 435/2
[58] Field of Search ................... 435/236, 2, 212

[56] References Cited

U.S. PATENT DOCUMENTS

| | | | |
|---|---|---|---|
| 4,456,590 | 6/1984 | Rubenstein | 514/2 |
| 4,721,777 | 1/1988 | Uemura et al. | 424/141.1 |
| 4,816,251 | 3/1989 | Seelich | 530/382 |
| 4,831,012 | 5/1989 | Estep | 514/6 |
| 4,876,088 | 10/1989 | Hirao et al. | 424/177.1 |
| 5,614,405 | 3/1997 | Eibl et al. | 435/367 |

*Primary Examiner*—Jon P. Weber
*Attorney, Agent, or Firm*—Michael J. Beck; James A. Giblin

[57] ABSTRACT

A method of rendering a biologically active protein composition substantially free of viruses is disclosed. The method includes the steps of preparing lyophilized samples of the protein composition having a given moisture content, determining a minimum or threshold moisture content which, when the composition is heated to pasteurizing conditions will result in at least a 3.2 $\log_{10}$ reduction in virus titer, and then heating the sample under pasteurizing conditions that will result in at least a 3.2 $\log_{10}$ reduction in virus titer while maintaining biological activity of the protein.

4 Claims, 3 Drawing Sheets

Fig._1

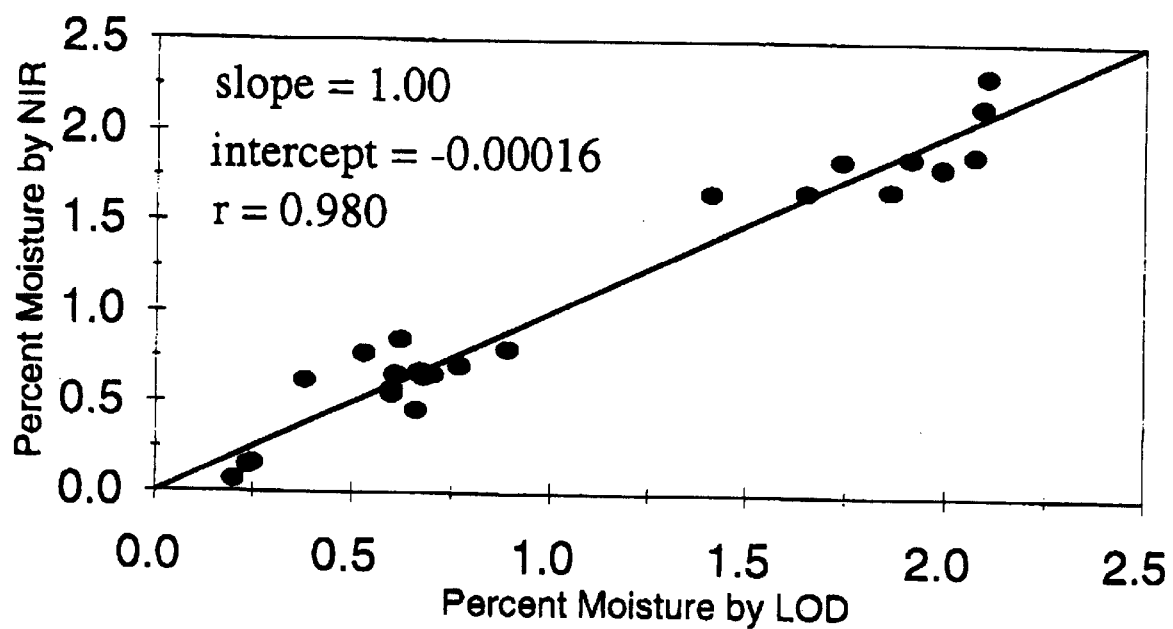
Fig._3

DRY-HEAT VIRAL INACTIVATION UNDER CONTROLLED MOISTURE CONDITIONS

BACKGROUND OF THE INVENTION

1. Field

This invention generally relates to inactivating viruses by heating in a lyophilized biological protein cake and specifically is concerned with determining the minimum amount of water content (moisture) in the protein matrix which is necessary for substantial reduction of virus titers in a biological protein matrix when heated under pasteurizing conditions.

2. Background

Many biologically active proteins are used to treat disease conditions in humans. However, preparations of active proteins isolated from human blood have an inherent hazard of transmitting virally-mediated diseases. It is therefore typical in the manufacture of the protein containing products to incorporate viral reduction or inactivation steps to yield safer products that decrease the risk of viral infection.

Virus titers may be reduced by of the method used to purify the protein. The Cohn-Oncley process used to purify IgG fractions from blood plasma has been found to yield proteins with reduced viral titers. See, for example, U.S. Pat. No. 4,762,714 to Mitra et al. See also Friedman et al., *Immunolog. Invest.* 24: 49–71 (1995) for a brief general discussion of reducing the infectivity of blood components.

Methods of inactivation of viruses by treatment with chemicals and/or heat are common in the art. For example, U.S. Pat. No. 4,540,573 to Neurath et al. (1985), incorporated herein by reference, describes treating protein-containing compositions with trialkylphosphate and detergent to inactivate viruses. Such solvent/detergent methods have gained acceptance as being efficacious in the inactivation of enveloped viruses with limited effects on blood product profile. Edwards et al., *Vox Sang.* 52: 53–59 (1987). See also U.S. Pat. No. 4,939,176 to Seng et al. (1990) for a discussion of various viral inactivation processes. U.S. Pat. No. 5,151,499 to Kameyama et al. (1992) adds a dry heat step to the trialkylphosphate/ detergent process to yield a greater reduction in virus titer. The effect of terminal dry heat treatment on non-enveloped viruses in coagulation factor concentrates is discussed in Hart et al., *Vox Sang,* 67:345–350 (1994).

Treatment of proteins with a mixture of solvent and detergent is widely used to prevent transmission of enveloped viruses by proteins derived from either biological or biotech sources. Piet et al., *Transfusion* 30: 592–98 (1990). This treatment is effective against those viruses which have a lipid-enveloped membrane, and is much less effective against those viruses which do not contain this structure. In recent years, transmission of at least two non-enveloped viruses by the use of a solvent/detergent treated biological product have been described. Hepatitis A virus, a non-enveloped RNA virus, was transmitted to patients using a Factor VIII product which had been treated with solvent detergent. Purcell et al., *Vox Sang.* 67 (supp. 4): 2–7 (1994). Factor VIII has also been implicated in the transmission of a non-enveloped parvovirus, B19, to humans. Lefrere et al., *Lancet* 343: 211–12 (1994).

Treatment of proteins with heat, either as dry powders (U.S. Pat. No. 4,456,590 to Rubinstein (1984); U.S. Pat. No. 4,495,278 to Thomas, (1985) ) or in an aqueous solution (U.S. Pat. No. 4,297,344 to Schwinn et al. (1981); U.S. Pat. No. 4,327,086 to Fukushima et al. (1982) ), has been used to extend the spectrum of anti-viral activity to include non-enveloped viruses. However, inactivation of non-enveloped viruses is generally more difficult than enveloped viruses and often requires longer treatment times or higher temperatures to assure complete inactivation. B19 was transmitted to patients by a Factor VIII product which was dry heat treated at 100° C. for 30 min. Santagostino et al., *Lancet* 343: 798 (1994). Solution pasteurization of FVIII, 10 hours at 63° C., was not sufficient to completely inactivate some non-enveloped viruses. Biesert et al., *Blood Coagul. Fibrinotysis* 6 (supp. 2): S48–54 (1995). Clearly, improved methods of viral inactivation are needed to maintain and improve the safety of biological products.

SUMMARY OF THE INVENTION

Our method of rendering a biologically active protein composition substantially free of viruses comprises the steps preparing lyophilized samples of the composition having a given water (or moisture) content, determining the minimum or threshold moisture content necessary to assure a substantial reduction in virus titer while maintaining biological activity when the composition is heated under pasteurizing conditions which assure substantial reduction of the viruses, selecting samples having that minimum moisture content and then subjecting those selected samples to the pasteurizing conditions. This method is non-destructive and can be correlated to currently used techniques such as loss on drying and Karl Fischer assays.

As used herein, substantial reduction in virus titer means at least about a 3.2 $\log_{10}$ unit reduction in virus titer, and more preferably at least about a 4 $\log_{10}$ unit reduction in virus titer.

As used herein, maintaining biological activity means demonstrating a measurable function or activity useful for an intended result (especially as opposed to the same protein in a denatured or useless state). The function, activity, or intended result may be, e.g., an enzymatic activity or a binding affinity. In the examples below, pasteurization conditions were selected within ranges that are known to be acceptable for maintaining such biological activity.

Pasteurization conditions mean heating to a temperature of at least 60° C. for at least 10 hours.

BRIEF DESCRIPTION OF THE FIGURES

FIG. 1: Scatter plot showing effect of exposure of samples of freeze-dried antihemophilic factor to atmospheric moisture for different time intervals.

FIG. 2: Scatter plot showing the correlation of percent moisture as measured by near infrared (NIR) technique with the percent moisture as measured by Karl Fischer titration.

FIG. 3: Scatter plot showing the correlation of percent moisture as measured by near infrared technique with the percent moisture as measured by Karl Fischer titration.

SPECIFIC EMBODIMENTS

A requirement for a minimal threshold level of moisture in order for efficient virus inactivation to occur during dry heat treatment of freeze-dried coagulation factor concentrates is described. Techniques used to determine moisture content during heating were loss on drying (LOD) and Karl Fischer (KF). The routinely used techniques were found to have errors induced as a result of sample preparation and handling. Therefore, a non-invasive, non-destructive method for determination of residual moisture content using near infrared spectrometry (NIR) was developed for freeze-dried antihemophilic factor (AHF). The method is based on the proportional O—H overtone signal in the region of the infrared spectrum and the level of residual moisture in the lyophilized cake. The determination can be made on the unopened vial and, therefore, the measurement is not influenced by interference from atmospheric moisture. NIR is a secondary technique and it relies on calibration against a primary technique, such as Karl Fischer or Loss-on-drying. Calibration equations were determined against both reference methods and these equations evaluated for the predictive efficiency. This method was used to evaluate the effect of moisture content on the efficiency of virus inactivation by dry heat at 80° C.

Materials and Methods

Viruses Used and Design of Viral Inactivation Experiments

The viruses chosen for this study and their attributes are summarized in Table 1. HIV-1 was evaluated as the clinically relevant virus representing HIV-1 and HIV-2. Bovine viral diarrhea virus (BVDV), an enveloped RNA virus, was selected as the relevant model for Hepatitis C virus. Pseudorabies virus (PRV), an enveloped DNA virus, was chosen as the model for the clinically relevant Herpes viruses: CMV, Epstein-Barr virus and Herpes simplex types 1, 2, 6 and 7. In addition, the non-enveloped RNA virus, Reovirus type 3 (Reo), was chosen as a model virus with resistance to physico-chemical reagents. Hepatitis A virus (HAV), strain HM175 was used as a clinically relevant virus for coagulation products and Porcine Parvo virus (PPV) was used to model for the human B 19 parvovirus. Both of these viruses (HAV and PPV) also are known to have high resistance to physico-chemical inactivation methods. The selection of viruses is in compliance with the recommendations published in the Note for Guidance on plasma derived Medicinal Products CPMP/BWP/269/95 published on 13 Mar, 1996.

Virus Quantitation Assays

Standard cell culture conditions were used for virus infectivity assays with RPMI 1640 or Eagle minimal essential medium (MEM) supplemented with non-essential amino acids, HEPES buffer (N-[2-Hydroxyethyl]piperazine-N'-[2-ethanesulfonic acid]), fetal bovine serum and antibiotics. The RPMI 1640 medium was used for the MT-4 cells only. Virus titers were quantitated by tissue culture infectious dose assays at 50% infectivity ($TCID_{50}$). $TCID_{50}$ titers were calculated by the method of Spearman-Kärber.

Ninety-six well micro titer plates were used with the appropriate confluent cells (BVDV in Bovine Turbinate (BT) cells, PRV in Rab-9 cells, Reo in BSC-1 or Vero cells, HAV in Fetal Rhesus Kidney (FRhK) cells and PPV in Swine Testicle (ST) cells. The Becker strain of PRV was used for studies where a higher titer was needed. The virus-spiked process inoculum was 0.1 mL per well. The test material was allowed to contact the cells for 1 hour at 37° C. to allow for virus adsorption. The material was removed and fresh MEM added to the wells. MEM was used for PRV, Reo, HAV and PPV. For BVDV, the MEM was supplemented with equine serum rather than fetal bovine serum. The plates were incubated 5 to 7 days at 36±2° C. HAV infected cells were incubated for 10 to 14 days at 36±2° C. After incubation, cell monolayers were observed microscopically for the presence of viral infection as indicated by cytopathic effect (CPE). After 5 to 7 days, CPE induced by BVDV, and PRV could easily be discerned by microscopic examination. CPE evidence of viral infection was observed at 7 days for Reo and PPV and at 10 to 14 days for HAV.

Apparatus

The Near Infrared spectrometer used was the NIR System model 6500 fitted with a Rapid Content Sampler (RCS) and the Vision-DA data acquisition software. The RCS sampling accessory allows for non-invasive analysis of a lyophilized product by directing the incident NIR beam through the base of the glass product vial which then penetrates the sample and is diffusely reflected in all directions. A portion of the reflected energy is collected by an array of six detectors arranged circumferentially about the incident beam fiber bundle.

Karl Fischer titrations were carried out using the Aquastar C3000 Coulometric titrator from EM Science. On this instrument iodine is generated electrochemically from iodine present in the cell. Iodine, methanol, sulfur dioxide, and an amine form the Karl Fischer reagent, which reacts quantitatively with water.

Reagents

Pyridine Free Coulomat Single Solution (EM Science) and Certified A.C.S. methanol (Fisher Scientific) were used in Karl Fischer determinations. Hydranal (Riedel-de Haën) was used as a water standard for the KF method.

Samples

Samples from production batches of Antihemophilic Factor (AHF) were obtained for moisture determination by the different methods evaluated. Experimental dry-heat treated samples of AHF (80° C. for 72–77 hours) were also obtained from experimental production runs and from the Virology Department. The samples obtained from the Virology Department were used for viral reduction evaluation of dry heat as a viral inactivation step.

Method

All samples were individually identified and scanned by NIR prior to analysis by either KF or LOD. The spectrometer was configured in a horizontal position. The spectral region monitored was 1100–2500 nm. Replicate sample scans (32) were automatically averaged to provide sample spectrum and the instrument was used on the reflectance x 1 setting. The samples were placed on the optical window over the detector mirrors. The vials were centered with a manually adjusted iris over the optic window. Samples were enclosed in the dark with a built-in cover during the measurement. The NIR scan was taken through the base of the sample vials.

To minimize the variability caused by factors such as the physical structure of the lyophilized cake and aberrations in the glass vials, second derivative spectra were calculated and the peak deflection from zero at 1930 nm used to calibrate against the reference moisture determination methods. Therefore, the term NIR relative moisture value refers to the second derivative peak deflection from zero for the water combination band at 1930 nm multiplied by a factor of 1000. The lyophilized cake in each test sample was pulverized before analysis by vortexing the vial for approximately 30 seconds.

Karl Fischer titrations were done with methanol extracts of the AHF lyophilized cake. Typically, methanol (5 mL or 10 mL) was injected into the vial and the vial mixed vigorously. The vials were then sonicated for 10 minutes at room temperature. The unopened vials were centrifuged at 3000 RPM for 30 minutes. A sample from the supernatant was, in each case, removed via syringe and injected into the Karl Fischer apparatus. The sample extraction methodology was designed to prevent sample exposure to atmospheric moisture. A typical injection size was 1.0 mL. The moisture content in the methanol used to extract the samples was done each time to determine a blank value.

A gravimetric method (Loss on Drying, LOD) was also used to determine moisture content. This procedure involved dispensing the lyophilized AHF cake into tared, stoppered glass containers. The unstoppered vials were placed in a drying chamber and the cake dried to a constant weight over phosphorous pentoxide under vacuum and heat. Measurement of the vial and cake weight were made before and after drying. The difference in mass was used to calculate the amount of water present. The gravimetric method measures surface water and loosely bound water of hydration.

Calibration of NIR moisture against Karl Fischer Titration

Samples of freeze-dried AHF with different moisture content were prepared by exposing vials from the same production batch to atmospheric moisture for different time intervals. The AHF lyophilized cake is hygroscopic and gains moisture in direct proportion to the time of exposure (FIG. 1). Samples were stoppered prior to analysis and the vials allowed to equilibrate overnight. The samples were evaluated for moisture content by NIR. Zero-order NIR spectra were transformed to second derivative spectra for quantitation. The same samples were then analyzed for moisture by Karl Fischer Titration. A calibration equation was then generated from the calibration set. The NIR/KF calibration equation was as follows:

$$\% \text{ moisture} = [(NIR \text{ Units}) \times 0.1115] - 1.037 \quad r = 0.98$$

Figure 2:
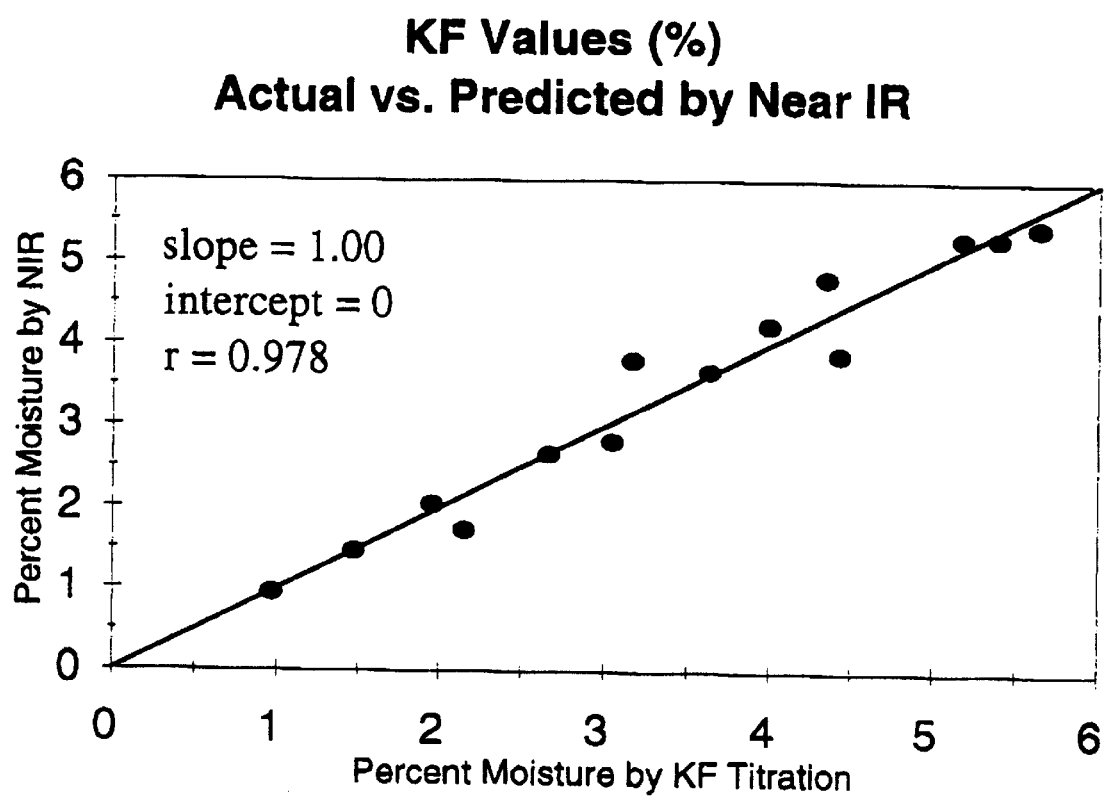

The calibration of NIR versus LOD is presented as a scatter plot in FIG. 2. The correlation coefficient shows a high degree of correlation between the NIR units and the LOD values obtained for the samples analyzed. This equation could then be used to estimate Karl Fischer moisture values using NIR evaluation.

Calibration of NIR moisture against Loss on Drying and Viral Inactivation results Samples of freeze-dried AHF were prepared by obtaining stoppers with different levels of moisture content and using these on vials of AHF prior to lyophilization. The lyophilized vials were then heated at 80° C. for various time intervals. The different incubation times resulted in varying moisture contents in the cake because of the moisture transfer rate from the stopper to the AHF cake.

The samples were evaluated for moisture content by NIR. Zero-order NIR spectra were transformed to second derivative spectra for quantitation. Samples were also analyzed by LOD. Replicates of three were averaged to obtain each calibration point. A calibration equation was then generated from the calibration set. The NIR/LOD calibration equation was as follows:

$$\% \text{ moisture} = [(NIR \text{ Units}) \times 0.0473] - 0.0411 \quad r = 0.98$$

The calibration of NIR versus LOD is presented as a scatter plot in FIG. 3. The correlation coefficient shows a high degree of correlation between the NIR units and the LOD values obtained, though with more scatter than in the NIR/KF calibration.

To evaluate the predictive ability of the NIR/LOD calibration curve AHF lyophilized samples from the Bayer Stability Program were evaluated for moisture content by NIR. The predicted LOD values were calculated from the NIR units and are compared to the experimental LOD values in Table 2. The predicted LOD values agree closely with the experimental values.

EXAMPLE 1

Table 3 shows the level of viral inactivation, using PRV as a model, obtained at the different time intervals and the moisture content at each timepoint. Both LOD and NIR data are shown. The data show that a 4.0 $\log_{10}$ reduction in viral load is obtained when the final moisture in the system is 2.0%. However, with a lower moisture content in the system as in the 0.7% final moisture vials, the degree of viral reduction is considerably less (i.e., 2.1 $\log_{10}$ reduction). Tables 4 and 5 also present additional experiments showing the viral inactivation obtained for PRV. All of the moisture values for these experiments were determined by LOD.

EXAMPLE 2

Table 6 shows the level of viral inactivation, using Hepatitis A as the model, obtained at the different time intervals and the moisture content as determined by LOD at each timepoint. The data show that when the moisture in the system is 0.8% or higher, a virus inactivation of greater than 4 $\log_{10}$ reduction may be obtained. However, if the moisture in the system was less than 0.8%, then the virus reduction after heating was less than 0.5 $\log_{10}$. There were four discrepant LOD moisture results in these experiments. These can be explained by data which show that a 0.5% increase in moisture can occur within 2 minutes of opening the vial and a 1.0% increase in moisture can occur within 5 minutes (FIG. 1). Therefore, any additional time taken in weighing out the lyophilized cake for LOD determination can result in a falsely elevated moisture result. Thus, the measurement of moisture least subject to introduction of error is the measurement of moisture in the vial by a method which does not require any manipulation of the cake or opening of the vial.

EXAMPLE 3

Table 7 shows the virus inactivation obtained at the different time intervals when PPV was used as the model. The moisture content as determined by LOD at each time point is shown. When the moisture was 0.8% or higher, the virus inactivation was above 3.2 $\log_{10}$ and was usually in the magnitude of 4 $\log_{10}$. However, when the moisture was low (0.5%) there was only a 2.5 $\log_{10}$ reduction in viral load (average of 2 experiments).

EXAMPLE 4

Table 8 shows the virus inactivation obtained at the different time intervals for HIV-1, Reovirus and for BVDV. The moisture content was measured by LOD only at the 72 hour time point for HIV-1 (1.3%) and the reduction was greater than 5.3 $\log_{10}$. Moisture determinations were done for the Reovirus and BVDV experiments at each of the time points. The moistures were near 1 % throughout the heating and the $\log_{10}$, reductions were more than 5 $\log_{10}$ for Reo and BVDV.

TABLE 1

Viruses Used for Inactivation Studies

| Attribute Virus | HIV-1 | BVDV | Pseudorabies | Hepatitis A | PPV | Reovirus type 3 |
|---|---|---|---|---|---|---|
| Strain | HIV-1 (IIIB) | NADL (ATCC VR-534) | PRV dl tk (ATCC VR-2074) or PRV Backer (Dupont/Merck) Wilmington, DE | HM 175 (Microbix Biosystems) Etobicoke, Canada or from Microbiological Associates Rockville, MD | NADL 2 (ATCC VR 742) | Abney (ATCC VR-232) |
| Nucleic acid | RNA | RNA | DNA | RNA | DNA | RNA |
| Enveloped | Yes | Yes | Yes | No | No | No |
| Size | 300 nm | 80–100 nm | 120–220 nm | 27–32 nm | 18–26 nm | 60–80 nm |
| Resistance to Physico-chemical agents | Low | Medium | Medium | High | Very High | High |
| Assay Systems | MT-4 cells (NIH) Bethesda, MD | BT cells (ATCC CRL 1390) | RAB-9 (ATCC CRL 1414) | FRhK4 (ATCC CRL 1688) or BSC-1 (ATCC CCL 26) | ST cells (ATCC CRL 1746) | BSC-1 cells (ATCC CCL 26) |

TABLE 2

Analysis of AHF samples in the QA Stability Program

| Lot | Near IR (units) | % Moisture LOD Experimental | LOD Predicted |
|---|---|---|---|
| 1 | 42.4 | 2.1 | 1.9 |
| 2 | 31.5 | 1.7 | 1.4 |
| 3 | 3.5 | 0.3 | 0.1 |
| 4 | 4.1 | 0.2 | 0.1 |
| 5 | 28.6 | 1.5 | 1.3 |
| 6 | 11.9 | 0.8 | 0.5 |
| 7 | 21.3 | 1.2 | 1.0 |
| 8 | 26.6 | 1.2 | 1.2 |
| 9 | 37.0 | 1.9 | 1.7 |

Samples were analyzed for moisture using NIR and the corresponding LOD values determined from a calibration curve (NIR versus LOD). The values obtained experimentally versus the predicted values are compared.

TABLE 3

EFFECT OF 80° C. DRY HEAT ON PRV IN FREEZE-DRIED AHF (10 mL fill)

| | TITER $LOG_{10}$ $TCID_{50}$/mL | | Moisture (%) Gravimetric | | Near Infrared (units) | |
|---|---|---|---|---|---|---|
| VIRUS-SPIKED TIMEPOINT | A | B | A | B | A | B |
| HBSS Control* | 5.3 | 5.9 | | | | |
| Pre-FD | 6.0 | 5.8 | | | | |
| Post-FD, 0 hour 80° C. | 4.7 | 4.5 | 0.2 | 0.5 | 3.46 | 16.6 |
| Post-FD, 24 hr 80° C. | 3.8 | 3.7 | 0.6 | 1.6 | 13.4 | 37.5 |
| Post-FD, 48 hr 80° C. | 4.0 | 3.8 | 0.7 | 2.0 | 14.2 | 42.2 |
| Post-FD, 72 hr 80° C. | 3.9 | 1.8 | 0.7 | 2.0 | 15.2 | 42.3 |
| $Log_{10}$ Reduction[1] | 2.1 | 4.0 | | | | |

*Hanks Balanced Salt Solution (Virus Spiked Media Control)
[1]$Log_{10}$ Reduction = Pre-FD (–) Post-FD, 72 hour 80° C.

TABLE 4

EFFECT of 80° C. DRY HEAT ON PRV IN FREEZE-DRIED AHF (MOISTURE ≥ 0.8%)

TITER $\text{Log}_{10}$ $\text{TCID}_{50}$/mL (Moisture by Loss on Drying)

| Expt. | A | B | C | D | E | F | G | H | I | J |
|---|---|---|---|---|---|---|---|---|---|---|
| Sample | | | | | | | | | | |
| HBSS | 5.5 | 5.5 | 5.2 | 5.2 | 5.7 | 5.7 | 6.6 | 6.6 | 6.6 | 6.6 |
| Pre-FD | 5.1 | 5.1 | 5.2 | 5.2 | 4.4 | 4.4 | 6.4 | 6.4 | 6.4 | 6.4 |
| Post-FD, 0 h 80° C. | 2.9 | 2.8 | 2.8 (0.3) | 3.3 (0.6) | 2.5 (0.9) | 2.5 (1.1) | 5.6 (1.0) | 5.4 (1.0) | 5.4 (0.4) | 5.5 (0.8) |
| 24 h 80° C. | 1.6 (1.1) | 1.6 (1.5) | 1.7 (0.7) | 1.6 (1.7) | 2.1 (1.3) | 1.2 (1.1) | 4.3 (1.6) | 3.9 (1.3) | 4.2 (1.0) | 3.8 (1.5) |
| 48 h 80° C. | 1.3 (1.1) | ≤1.0 (1.6) | 2.1 (0.9) | 2.0 (1.9) | 1.8 (1.6) | 1.5 (1.3) | 2.6 (1.5) | 2.9 (1.3) | 3.9 (1.3) | 1.6 (1.1) |
| 72 h 80° C. | 1.0 (1.1) | ≤1.0 (1.6) | 1.7 (0.8) | 1.4 (1.8) | 1.0 (1.3) | 1.0 (1.4) | 2.4 (1.1) | 2.9 (1.5) | 3.6 (1.5) | 2.7 (1.3) |
| $\text{Log}_{10}$ Reduction | 4.1 | ≥4.1 | 3.5 | 3.8 | 3.4 | 3.4 | 4.0 | 3.5 | 2.8 | 3.7 |
| Average $\text{Log}_{10}$ Reduction | | | | | 3.93 ± 0.98 (1.37 ± 0.32) | | | | | |

TABLE 5

EFFECT of 80° C. DRY HEAT ON PRV IN FREEZE-DRIED AHF (MOISTURE ≤ 0.7%)

$\text{Log}_{10}$ $\text{TCID}_{50}$/mL (Moisture by Loss on Drying)

| Expt. | A | B | C | D | E |
|---|---|---|---|---|---|
| Sample | | | | | |
| HBSS | 5.5 | 5.6 | 5.7 | 5.7 | 5.7 |
| Pre-FD | 5.5 | 5.4 | 4.4 | 5.9 | 5.9 |
| Post FD 0 h 80° C. | 3.6 (0.2) | 4.5 (0.4) | 2.8 (0.3) | 5.0 (0.2) | 5.2 (0.1) |
| 24 h 80° C. | 3.0 (0.5) | 3.7 (0.4) | 1.7 (0.4) | 4.3 (0.2) | 3.9 (0.3) |
| 48 h 80° C. | 2.6 (0.2) | 3.3 (1.1) | 1.8 (0.4) | 3.9 (0.4) | 3.7 (0.5) |
| 72 h 80° C. | 3.0 (0.5) | 2.9 (0.7) | 1.6 (0.6) | 3.7 (0.4) | 3.1 (0.5) |
| $\text{Log}_{10}$ Reduction | 2.5 | 2.5 | 2.8 | 2.2 | 2.8 |
| Average $\text{Log}_{10}$ Reduction | | | 2.56 ± 0.25 (0.54 ± 0.11) | | |

TABLE 6

EFFECT of 80° C. DRY HEAT ON HAV IN FREEZE-DRIED AHF $\text{Log}_{10}$ $\text{TCID}_{50}$/mL (Moisture by Loss on Drying)

| | Moisture ≥ 0.8% | | | | | (Moisture ≤ 0.8%) | | | | |
|---|---|---|---|---|---|---|---|---|---|---|
| Expt. | A | B | C | D | E | F | G | H | I | J |
| Sample | | | | | | | | | | |
| HBSS | 5.2 | 4.9 | 4.9 | 5.3 | 5.3 | 4.2 | 4.2 | 4.2 | 5.0 | 5.4 |
| Pre-FD | 5.6 | 5.6 | 6.0 | 5.5 | 5.3 | 4.2 | 4.2 | 4.2 | 4.6 | 5.5 |
| Post FD 0 h 80° C. | 3.1 (0.6) | 3.4 (0.6) | 3.0 (0.7) | 4.3 (0.5) | 4.3 (0.5) | 4.9 (0.2) | 4.5 (0.3) | 4.2 (0.1) | 4.1 (0.4) | 5.7 (0.2) |
| 24 h 80° C. | ≤1.3 (0.7) | ≤1.3 (1.5) | ≤1.3 (1.2) | ≤1.3 (0.7) | ≤1.3 (0.7) | 4.9 (0.8) | 4.7 (1.4)* | 4.5 (0.1) | 4.4 (0.1) | 5.4 (0.4) |
| 48 h 80° C. | ≤1.3 (0.8) | ≤1.3 (1.8) | ≤1.3 (1.4) | ≤0.7 (1.0) | ≤0.7 (1.0) | 4.7 (0.4) | 4.4 (0.4) | 4.0 (1.3)* | 5.0 (0.4) | 5.4 (0.5) |
| 72 h 80° C. | ≤1.3 (0.8) | ≤1.3 (1.8) | ≤1.3 (1.3) | ≤0.7 (1.3) | ≤0.7 (1.3) | 4.3 (0.4) | 4.1 (0.6) | 4.1 (1.5)* | 4.7 (1.0)* | 5.1 (0.6) |
| $\text{Log}_{10}$ Reduction | ≥4.3 | ≥4.3 | ≥4.7 | ≥4.8 | ≥4.6 | 0 | 0.1 | 0.1 | 0 | 0.4 |
| Average $\text{Log}_{10}$ Reduction | ≥4.54 ± 0.23 (1.3 ± 0.35) | | | | | 0.12 ± 0.16 (0.53 ± 0.11)* | | | | |

*Moisture results for duplicate vials - Discrepant results thought to be due to sample handling

TABLE 7

EFFECT of 80° C. DRY HEAT ON PPV IN FREEZE-DRIED AHF $Log_{10}$ $TCID_{50}$/mL (Moisture by Loss on Drying)

| | (Moisture $\geq$ 0.8%) | | | | | (Moisture < 0.8%) | |
|---|---|---|---|---|---|---|---|
| Expt. | A | B | C | D | E | F | G |
| Sample | | | | | | | |
| HBSS | 5.4 | 5.4 | 6.2 | 6.6 | 6.7 | 6.3 | 5.8 |
| Pre-FD | 5.4 | 5.4 | 6.2 | 6.7 | 6.2 | 6.3 | 6.1 |
| Post FD | 4.4 (0.3) | 4.2 (1.2) | 6.3 (0.1) | 6.7 (0.8) | 6.6 (0.8) | 6.4 (0.1) | 6.4 (0.1) |
| 0 h 80° C. | | | | | | | |
| 24 h 80° C. | $\leq$1.3 (1.0) | 1.9 (2.5) | 3.6 (0.6) | $\geq$4.7 (1.4) | $\geq$4.5 (1.4) | $\geq$4.7 (0.1) | $\geq$3.9 (0.1) |
| 48 h 80° C. | NT | NT | 2.9 (0.8) | 3.1 (1.2) | 3.8 (1.2) | $\geq$4.6 (0.2) | 4.2 (0.2) |
| 72 h 80° C. | 1.5 (0.8) | $\leq$1.3 (2.6) | 2.4 (0.8) | 3.1 (0.9) | 3.0 (0.9) | 3.7 (0.5) | 3.7 (0.5) |
| $Log_{10}$ Reduction | 3.9 | $\geq$4.1 | 3.8 | 3.6 | 3.2 | 2.6 | 2.4 |
| Average $Log_{10}$ Reduction | | | 3.72 $\pm$ 0.34 | | | 2.5 $\pm$ 0.14 | |

NT - Not tested

TABLE 8

EFFECT of 80° C. DRY HEAT ON HIV-1, BVDV and Reo IN FREEZE-DRIED AHF $Log_{10}$ $TCID_{50}$/mL (Moisture by Loss on Drying)

| Virus | HIV-1 | | | BVDV | | | Reo | | |
|---|---|---|---|---|---|---|---|---|---|
| Expt. | A | B | C | A | B | C | A | B | C |
| Sample | | | | | | | | | |
| HBSS | 6.3 | 5.9 | 5.6 | 6.5 | 6.1 | 6.1 | $\leq$7.7 | 6.8 | 6.6 |
| Pre-FD | 6.1 | 6.1 | 6.1 | 6.3 | 6.3 | 6.4 | 7.5 | 6.8 | 7.1 |
| Post FD | | | | | | | | | |
| 0 h 80° C. | 5.7 | 5.9 | 5.2 | 6.0(0.7) | 6.1 | 6.1 | 5.8(0.0) | 5.4(0.3) | 5.5 |
| 4 h 80° C. | $\leq$0.8 | $\leq$0.8 | $\leq$0.8 | 3.5(0.5) | 4.4 | 5.6 | 3.7(0.1) | 3.9(0.5) | 3.8 |
| 8 h 80° C. | $\leq$0.8 | $\leq$0.8 | $\leq$0.8 | 2.4(0.7) | 2.5 | 2.6 | 3.5(0.5) | 3.7(0.7) | 3.0 |
| 16 h 80° C. | $\leq$0.8 | $\leq$0.8 | $\leq$0.8 | 1.5(1.0) | 1.4 | 1.6 | 2.3(0.6) | 2.5(0.9) | 2.3 |
| 24 h 80° C. | $\leq$0.8(1.3) | $\leq$0.8 | $\leq$0.8 | $\leq$1.3(1.1) | 1.3 | 1.3 | 1.3(0.5) | 1.4(1.1) | 1.5 |
| 48 h 80° C. | NT | NT | NT | $\leq$1.3(1.1) | $\leq$1.3 | 1.3 | $\leq$1.3(0.4) | $\leq$1.3(1.3) | 1.6 |
| 72 h 80° C. | NT | NT | NT | $\leq$1.3(0.5) | $\leq$1.3 | $\leq$1.3 | $\leq$1.3(0.7) | $\leq$1.3(1.3) | 1.8 |
| $Log_{10}$ Reduction | $\geq$5.3 | $\geq$5.3 | $\geq$5.3 | $\geq$5.0 | $\geq$5.0 | $\geq$5.1 | $\geq$6.2 | $\geq$5.5 | 5.3 |
| Average $Log_{10}$ Reduction | | $\geq$5.3 | | | $\geq$5.0 | | | 5.7 $\pm$ 0.47 | |

NT - Not tested

CONCLUSION

These data show that in order to assure an adequate level of viral reduction resulting from dry heating, the threshold moisture level must be established and assured. Previously known assay methods are insufficient in precision to guarantee a precise level of moisture for virus kill because of the degree of sample manipulation required for the assays. NIR technology offers a practical alternative for rapid, non-invasive, and non-destructive analysis to determine moisture content in lyophilized biological products with high precision and accuracy. This technology can be applied to virus inactivation methods for dry heat treating lyophilized products such that the minimum level of moisture can be assured for all production vials.

The above examples are intended to illustrate the invention and it is thought variations will occur to those skilled in the art. Accordingly, it is intended that the scope of the invention should be limited only by the claims below.

What is claimed is:

1. In a method for substantially reducing the virus titer of a lyophilized biologically active protein containing composition, the composition having a residual moisture content, the method comprising the steps of heat treating the composition in a dry state under controlled conditions of temperature and time, the improvement comprising the steps of (a) establishing a threshold moisture level necessary to assure at least a substantial reduction in virus titer when the composition is heat treated under pasteurizing conditions and (b) then applying the heat treatment under at least said threshold moisture level to assure at least a substantial reduction in virus titer while maintaining biological activity of the protein.

2. A method of assuring a substantial reduction of virus titer in at least one sample of a plurality of lyophilized biologically active protein containing compositions, the compositions having a residual moisture content, the method comprising (a) determining the residual moisture content of samples of the compositions and selecting only samples having a threshold moisture content necessary to assure at least a substantial reduction in virus titer when subjected to pasteurizing conditions and (b) heating the selected compositions under the pasteurizing conditions sufficient to assure at least the substantial reduction in virus titer while maintaining biological activity of the protein.

3. The method of claim 2 wherein the threshold moisture content is about 0.8 weight %.

4. The method of claim 1 wherein the substantial reduction in virus titer is a reduction of at least 3.2 $\log_{10}$ virus titer.

* * * * *